US005620692A

United States Patent [19]
Potter et al.

[11] Patent Number: 5,620,692
[45] Date of Patent: Apr. 15, 1997

[54] OAT OIL COMPOSITIONS WITH USEFUL COSMETIC AND DERMATOLOGICAL PROPERTIES

[75] Inventors: Richard C. Potter, Seeley Lake; James M. Castro; Lori C. Moffatt, both of Missoula, all of Mont.

[73] Assignee: Nurture, Inc., Missoula, Mont.

[21] Appl. No.: 172,485

[22] Filed: Dec. 23, 1993

[51] Int. Cl.$^6$ .................................................. A61K 7/00
[52] U.S. Cl. .................................. 424/401; 424/195.1
[58] Field of Search ........................... 424/401, 195.1; 530/370, 372; 514/783, 784, 785; 252/107

[56] References Cited

U.S. PATENT DOCUMENTS

| | | | |
|---|---|---|---|
| 2,176,037 | 10/1939 | Musher | 426/543 |
| 2,355,097 | 8/1944 | Musher | 426/542 |
| 2,739,163 | 3/1956 | Appuhn | 554/156 |
| 2,975,066 | 3/1961 | Baker et al. | 426/543 |
| 3,988,436 | 10/1976 | Loo | 424/59 |
| 4,014,995 | 3/1977 | Juliano et al. | 514/783 |
| 4,028,468 | 6/1977 | Hohner et al. | 426/436 |
| 4,169,090 | 9/1979 | Murray et al. | 530/370 |
| 4,211,801 | 7/1980 | Oughton | 426/430 |
| 4,238,509 | 12/1980 | Evans et al. | 514/777 |
| 4,376,133 | 3/1983 | Farnand | 426/656 |
| 4,530,788 | 7/1985 | Chang | 530/370 |
| 4,671,892 | 6/1987 | Bereiter | 252/370 |
| 4,677,065 | 6/1987 | Büchbjerg et al. | 530/370 |
| 4,793,990 | 12/1988 | Grollier et al. | 424/59 |
| 4,883,659 | 11/1989 | Goodman et al. | 424/78 |
| 5,026,548 | 6/1991 | Evans et al. | 424/195.1 |
| 5,093,109 | 3/1992 | Mausner | 514/783 |
| 5,308,618 | 5/1994 | Konno et al. | 424/195.1 |
| 5,312,636 | 5/1994 | Myllymaki et al. | 426/417 |
| 5,409,716 | 4/1995 | Trumbetas et al. | 424/7 |

FOREIGN PATENT DOCUMENTS

| | | |
|---|---|---|
| 59-167508 | 3/1983 | Japan. |
| 8901294 | 2/1989 | WIPO. |

OTHER PUBLICATIONS

Baker, et al. "Water–Soluble Inhibitor(s) of Tumor Respiration Formed from Ultraviolet–induced Oxidation of Linoleic and Linolenic Acids" *J. of Lipid Res.* 7: 249–356 (1966).

Baker, et al. "Water–Soluble Products of UV–Irradiated Autoxidized Linoleic and Linolenic Acids" *J. of Lipid Res.* 7: 341–348 (1966).

Chedekel, et al. "Sunlight, Melanogenesis and Radicals in the Skin" *Lipids* 23(6): 587–591 (1988).

Forsell, et al. "Antioxidative Effects of Oat Oil and its Fractions" *Chem. Abstracts* 113: 189918w (1990).

Mihara, et al. "Thiobarbituric Acid Value on Fresh Homogenate of Rat as a Parameter of Lipid Peroxidation in Aging, $CCl_4$ Intoxication and Vitamin E Deficiency" *Biochemical Medicine* 23: 302–311 (1980).

Niki, et al. "Inhibition of Oxidation of Methyl Linoleate in Solution by Vitamin E and Vitamin C" *J. of Biol. Chem.* 259(7): 4177–4182 (1984).

Sugiyama, et al. "Lipid Peroxidation and Radical Formation in Methyl Linoleate Following Ultraviolet Light Exposure" *J. of Dermatology* 11: 455–459 (1984).

*Primary Examiner*—Thurman K. Page
*Assistant Examiner*—Sharon Howard
*Attorney, Agent, or Firm*—Knobbe, Martens, Olson & Bear

[57] ABSTRACT

A process to prepare oat oil compositions with beneficial dermatological properties is disclosed. Formulations incorporating the oat oil compositions have antioxidant and other dermatologically beneficial properties. The compositions, either alone or in cosmetic formulations including lipid emulsions, inhibit ultraviolet irradiation-induced lipid peroxidation. The methods have applications in the cosmetic industry for inhibiting ultraviolet irradiation-induced skin damage and other beneficial dermatological properties. The formulations of the invention also are potent antioxidants.

23 Claims, 5 Drawing Sheets

OAT OIL COMPOSITIONS WITH USEFUL COSMETIC AND DERMATOLOGICAL PROPERTIES

This research was supported by United States Department of Agriculture agreement number 92-33610-7245. The government may have certain rights in this invention.

FIELD OF THE INVENTION

The present invention relates to the use of relatively crude oat oil in cosmetic and dermatological applications. More specifically, the oat oil compositions of the present invention are useful as antioxidants, antiperoxidation agents, antiaging agents, and antiwrinkle agents when applied to the skin, or generally to the human body.

BACKGROUND OF THE INVENTION

Oats (Avena sativa) have unique characteristics which set them apart from other cereal grains. Oats contain a significantly higher protein concentration (15–20%) than other cereal grains (Peterson and Brinegar, (1986) in *Oats: Chemistry and Technology*, F. H. Webster, ed., Am. Assoc. of Cereal Chemists, Inc., St. Paul, Minn.). Oats also have one of the highest oil contents of the cereal grains.

Similar to other cereal grains, oat oil can be isolated from the oats by extraction with organic solvents. Oat oil has been noted for its variety and concentration of antioxidants (Youngs, (1986), ibid.; Hoseney, (1986) *Principles of Cereal Science and Technology*, F. H. Webster, ed., American Association of Cereal Chemists, Inc., St. Paul, Minn.); Hammond, (1983) in *Lipids in Cereal Technology*, P. J. Barnes, ed., Academic Press, New York). The peroxide value of a lipid provides an indication of the amount of rancidity-inducing peroxide radicals present in the lipid and is inversely correlated with product stability. The peroxide value is a titration which measures the levels of organic peroxides present in a fat and is a measure of the oxidative stability of the fat, and, thus, its antioxidant effectiveness.

Freshly-prepared oat oil has a peroxide value of zero, while oils from other cereal grains have higher peroxide values. When the peroxide value of an oil reaches about 20 or 25, the oil is usually contains detectable rancidity in its taste or odor. Two of the principle antioxidants found in oats are esters of caffeic and ferulic acid which exhibit some structural similarity to the synthetic antioxidants butylated hydroxyanisole (BHA) and butylated hydroxytoluene (BHT). In addition, other antioxidants including tocopherols, tocotrienols, and o-aminophenol and its esters are also found in oats and several of these are probably present in the extracted oil.

As mentioned above, oil is generally recovered from cereal grains by extraction with organic solvents, typically hexanes or heptanes. The solvent is then eliminated by evaporation, typically distillation. The resulting crude vegetable oil contains numerous fine particles consisting predominantly of proteins (20–60%). The crude oil is then subjected to various refining steps including filtration to remove particulates, water washing to remove solids and gums, acid washing to remove phosphatides, alkali neutralization to remove free fatty acids, chilling ("winterization") to remove high-melting triglycerides, decolorizing ("bleaching") with activated bleaching earth or activated carbon, and deodorization by heating under high vacuum. Hydrogenation can also be performed to increase stability by increasing the chemical saturation state of the fatty acids in the oil.

A variety of oils have been used in dermatological formulations. For example, the use of both rice bran oil (U.S. Pat. No. 3,988,436 to Loo) and coffee bean oil (U.S. Pat. No. 4,793,990 to Grollier et al.) as sunscreen agents has been described. The Loo and Grollier et al. patents discuss the UV absorption properties of the oils. However, the patents do not indicate antioxidant action.

Nevertheless, it is established that vegetable seeds, cereal grains, and oils derived therefrom contain compounds that exhibit certain antioxidant activities. For example, the extracts from cereal grains treated with polar organic solvents, such as methanol, ethanol, and butanol, contain antioxidant activity (U.S. Pat. No. 2,975,066 to Baker et al.; U.S. Pat. No. 2,355,097 to Musher; Forsell et al., (1990) *Chem. Abstracts*, 113:189918w). When nonpolar organic solvents are used, the resulting extracts do not contain as high an antioxidant activity (U.S. Pat. No. 2,176,037 to Musher). Further, the prior art only teaches the use of highly purified oils for use as antioxidants (U.S. Pat. No. 2,355,097 to Musher; U.S. Pat. No. 4,211,801 to Oughton). There is no teaching in the prior art of the use of crude, largely unrefined oat oil as an antioxidant.

Antioxidants are important in skin care products since a major cause of photoaging is believed to be uncontrolled lipid peroxidation in the skin. This peroxidation is caused by the generation of free radicals when photons of ultraviolet light strike the skin. These radicals cause damage to vital skin components and also induce localized inflammatory responses.

Ultraviolet light or chemical initiators of oxidation have been shown to cause lipid peroxidation of methyl linoleate with free radical formation (Sugiyama et al., (1984) *J. Dermatol.*, 5:455–459; Baker and Wilson, (1966) *J. Lipid Res.*, 7:349–356; Baker and Wilson, (1966) *J. Biol. Res.*, 7:341–348). The addition of antioxidants to this system has been shown to inhibit the peroxidation of methyl linoleate and result in a decrease in the formation of lipid peroxidation by-products such as malonyldialdehyde (MDA) (Niki et al., (1984) *J. Biol. Chem.*, 7:4177–4182; Chedekel and Zeise, (1988) *Lipids*, 23:587–591).

Despite the variety of oils available for use in dermatological compositions and their many apparent functions, there remains a need for readily available, naturally-occurring, non-toxic oil compositions that are easily isolatable and are effective in multiple dermatological applications, such as in antioxidant, antiperoxidation, antiaging, and antiwrinkle applications.

SUMMARY OF THE INVENTION

In one aspect of the present invention, there is provided a method for producing a cosmetic formulation comprising the steps of providing an aqueous phase, providing a lipophilic phase comprising crude oat oil, providing an amount of an emulsifier effective to form an emulsion of the aqueous phase and the lipophilic phase, mixing the aqueous phase, the lipophilic phase, and the emulsifier to form a mixture, and agitating the mixture such that an emulsion is formed. In a preferred embodiment, the crude oat oil is produced by a process consisting essentially of the following steps contacting oats with organic solvent to extract oat oil, evaporating the solvent from the oat oil, washing the oat oil, and deodorizing the oat oil fraction under vacuum at a temperature below about 120° C. In another preferred embodiment, the first oil fraction is washed at a temperature between about 50° C. and about 100° C. In a particularly preferred embodiment, the oil is washed at a temperature between about 70° C. and about 75° C.

In certain preferred embodiments, the extracting step comprises one or more of the following steps mixing the oats with an organic solvent to extract the oil from the oats, removing the solvent from the oats after a period of time, evaporating the solvent to obtain a first oat oil fraction, clarifying the first oat oil fraction by heating the first oat oil fraction to between about 40° C. and about 120° C. and adding a minor amount of water while maintaining the temperature within the range of between about 40° C. and about 120° C. In a preferred embodiment, the first oil fraction is heated to a temperature between about 50° C. and about 100° C. In a particularly preferred embodiment, the oil is heated between about 70° C. and about 75° C. and any solid material is removed to obtain an second oat oil fraction, followed by drying the second oat oil fraction by heating under vacuum to a temperature between about 80° C. and about 120° C. to obtain a dried oat oil fraction.

In another preferred embodiment, the second oat oil fraction is heated to a temperature between 90° C. and 110° C. In a most preferred embodiment, the second oat oil fraction is heated to a temperature between 100° C. and 105° C. Preferably deodorization is of the dried oat oil fraction is accomplished under vacuum at a temperature between about 15° C. and about 120° C. In a particularly preferred embodiment, the oil is deodorized under vacuum at a temperature between about 20° C. and about 100° C.

Preferably, the solvent is hexane, the oat oil is washed with either water or phosphoric acid after the solvent evaporation step. In a preferred embodiment, the oil has a peroxide value of between zero and 20 or 25 for a period of time between zero and 50 days at 60° C. In highly preferred embodiments, the oat oil has a peroxide value of about zero for about 50 days at 60° C.

Preferably, the emulsifier is a substantially chemically intact proteinaceous particulate material derived from seeds of legumes and grains. Most preferably, the seeds are selected from the group of canola, beans, oats, rape seed or soya.

In a preferred embodiment, the oat oil is included in an amount effective to inhibit oxidation when applied to skin. Preferably, the oat oil is included in an amount effective to inhibit lipid peroxidation in skin when applied to skin and when the skin is exposed to ultraviolet radiation.

Advantageously, the oat oil is obtained from a crude oat oil fraction that is derived from the extraction of oats with an organic solvent. Most preferably, the organic solvent is an isomeric mixture of hexanes and the oat oil is washed with either water or an aqueous solution of phosphoric acid.

Alternatively, there is provided oat oil derived from a crude oat oil fraction that has been subjected to low temperature vacuum deodorization.

In another aspect of the present invention, there is provided a method of inhibiting skin lipid peroxidation in response to ultraviolet irradiation of the skin by applying an oat oil composition to the skin prior to ultraviolet irradiation of the skin. Preferably, the oat oil has been obtained by extraction of oats with an organic solvent, most preferably, the organic solvent is an isomeric mixture of hexanes and the oat oil has been derived from a crude oat oil fraction that has been washed with either water or an aqueous solution of phosphoric acid. Advantageously, the oat oil has been derived from a crude oat oil fraction that has been subjected to low temperature vacuum deodorization.

In still another embodiment of the invention, there is provided a method of preparing a dermatologically effective soap by cold saponifying a crude oat oil with alkali. Preferably, the oat oil is a crude oil fraction produced by the process described above.

In another aspect of the present invention, there is provided crude oat oil prepared according to the process described above.

Yet another embodiment of the invention is crude oat oil, the improvement comprising skin lipid peroxidation-inhibiting activity, UVB irradiation-blocking ability, and a reduced peroxide value. For example, in a preferred embodiment, the oil has a peroxide value of between zero and 20 or 25 for a period of time between zero and 50 days at 60° C. In a highly preferred embodiment, the oil has a peroxide value of zero for about 50 days. In another highly preferred embodiment, the compositions have greater skin lipid peroxidation-inhibiting activity than linoleic acid.

DETAILED DESCRIPTION OF THE PREFERRED EMBODIMENTS

Figure 1:
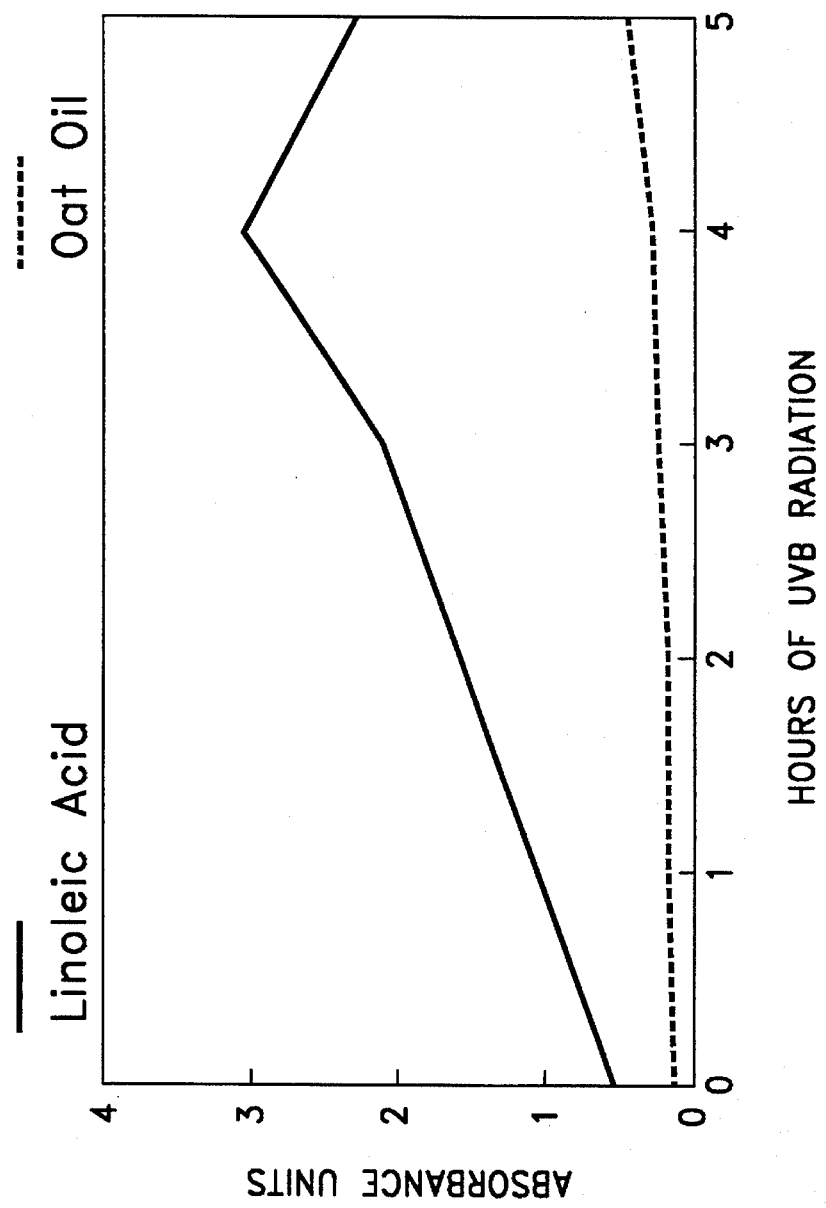
FIGS. 1–4 show the UVB-induced lipid peroxidation of oat oil and linoleic acid (65% purity) at concentrations of 100%, 5%, 10% and 25%, respectively. Hours of UVB irradiation are shown on the x-axis and absorbance at 535 nm is shown on the y-axis.
Figure 2:
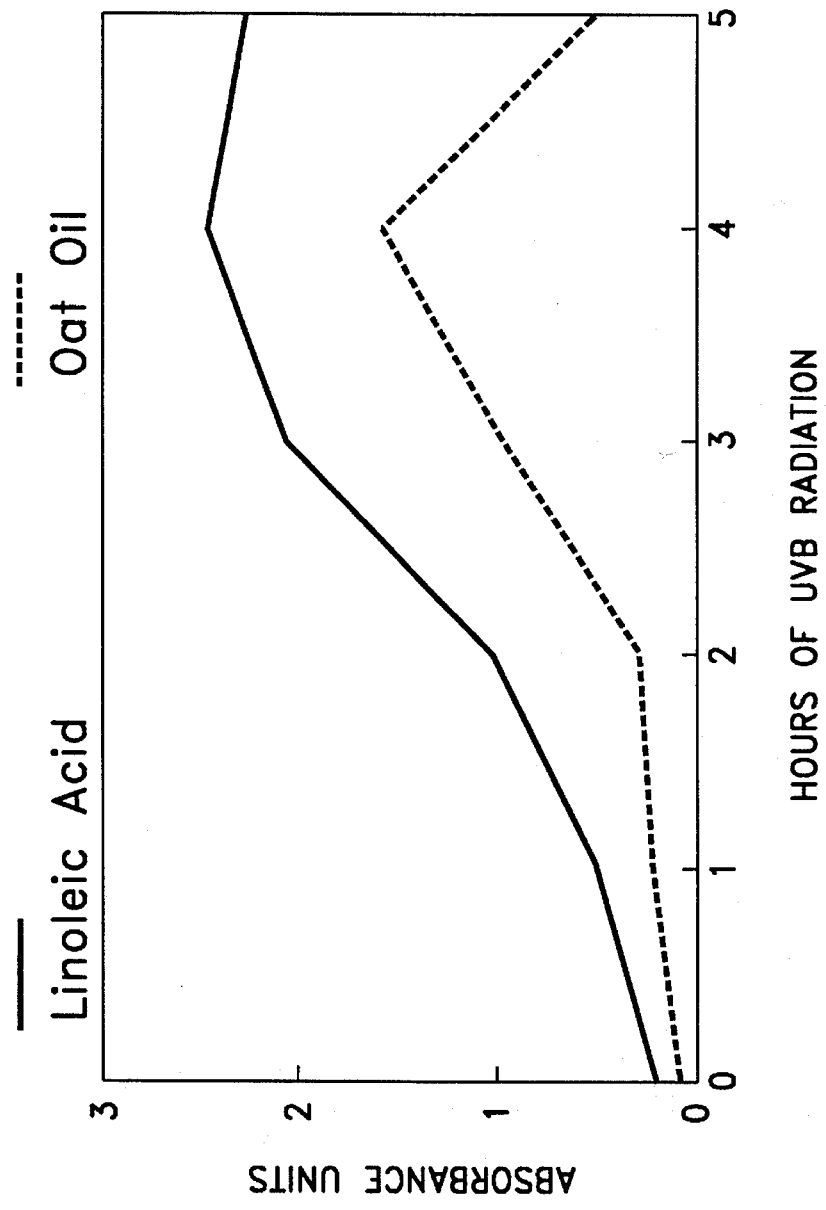
Figure 3:
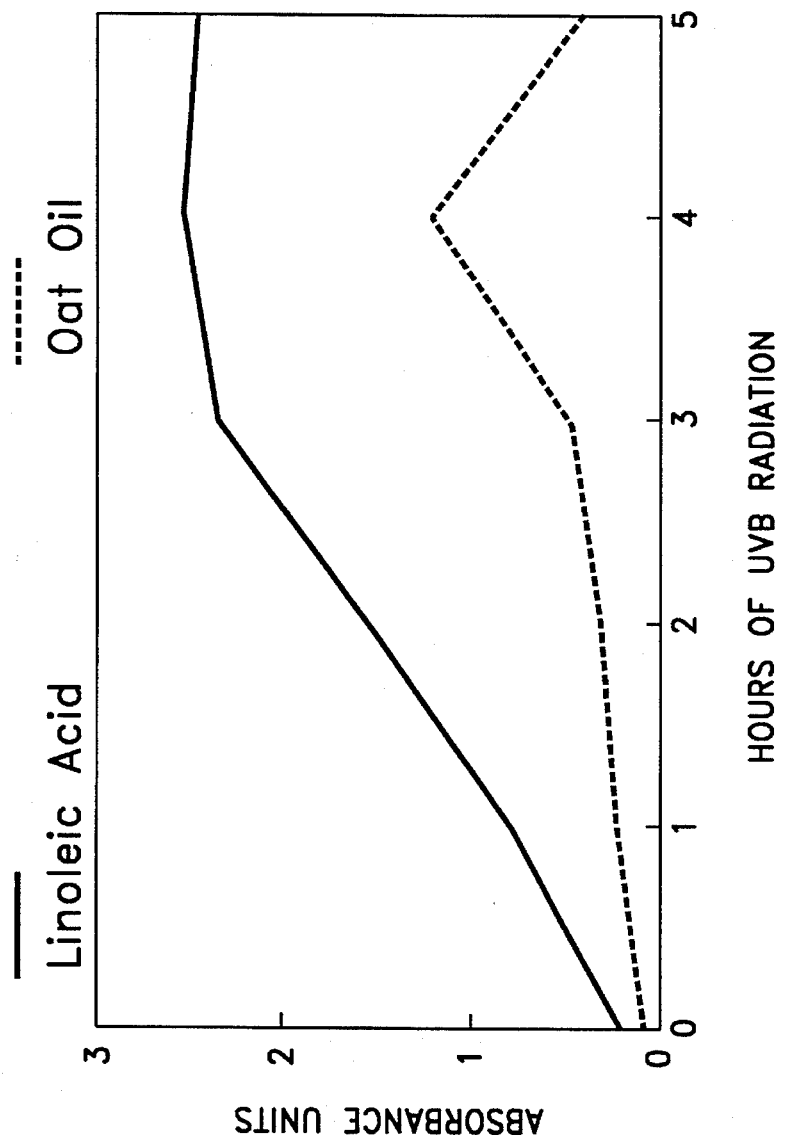
Figure 4:
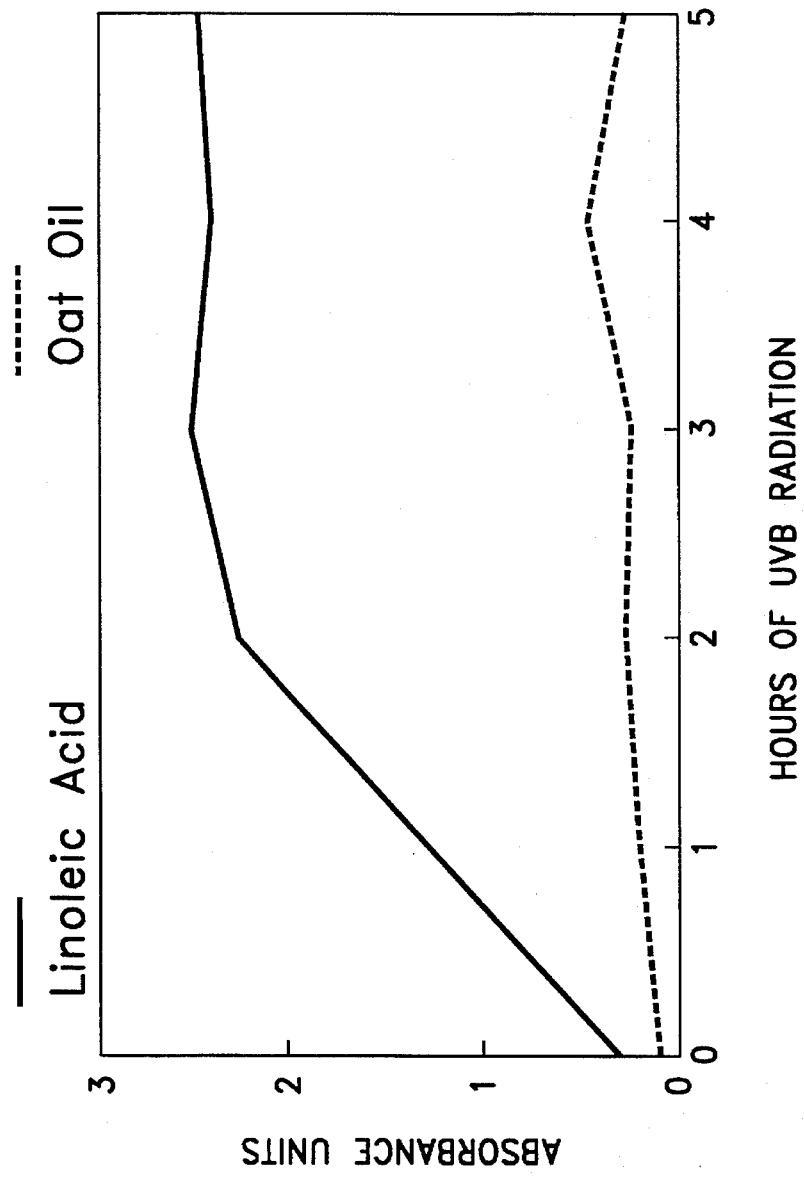

The present invention relates, in its broadest sense, to oat oil compositions that are effective cosmetic and dermatological agents. For example, the compositions of the invention are effective in sunscreen formulations to absorb the sun's ultraviolet irradiation and to inhibit lipid peroxidation in the skin upon exposure to ultraviolet irradiation. Further, the compositions are expected, because of their superior antioxidant properties, to act as antiwrinkle/antiaging compositions. Moreover, the oat oil compositions can be used in lotions, soaps, or other cosmetically and dermatologically acceptable forms with great success and without irritation. In addition, to skin care, the compositions of the invention are useful in other cosmetic applications such as lip balms and hair care.

Unexpectedly, the oat oil compositions of the invention can be prepared from a relatively crude oat oil extract. Such crude oat oil extracts also act as antioxidants in enhancing the storage stability of lipid-containing food products (See U.S. patent application Ser. No. 08/165,364, filed Dec. 10, 1993). As used herein, "crude oat oil" shall mean oat oil that has been solvent extracted from oats, and has been optionally been exposed to filtration (such as sodium sulfate filtration), centrifugation, water washing, phosphoric acid washing, and low temperature and/or vacuum deodorization, but that has not been purified by winterization, bleaching, alkali washing, decolorizing, high temperature deodorization or hydrogenation, except to the extent that any of the aforementioned steps can be considered as such.

The oat oil compositions of the present invention increase the stability of oils and skin lipids. This effect is particularly observable in shelf life studies, as well as when the compositions of the present invention are subjected to ultraviolet irradiation. Even relatively minor amounts of the compositions are effective.

In addition to, or possibly in connection with, the antioxidant properties of the oat oil compositions of the invention, the compositions exhibit antipyretic effects. For example, the compositions of the present invention can be applied to rashes or wounds in or on the skin and they will cut down irritation in the rash or wound, if not heal the rash or wound. Moreover, the compositions are nonirritating, pleasant, and have a soothing feel. Lotions prepared with the compositions of the invention feel good on application to the skin and do not leave the skin feeling dry or scaly after removal. However, the skin does not feel oily or greasy either. Rather, a natural, vibrant luster and/or sheen is seen and felt upon application.

In accordance with the invention, the oil is isolated from oats by extraction with an organic solvent using minimal refining steps. Any organic solvent effective in extracting lipophilic compounds from oats may be used provided it can be separated from the oil after the extraction process. Among the preferred solvents are low boiling, highly refined, relatively nonpolar petroleum fractions such as n-hexane and n-heptane ("paraffin" solvents), or isomeric mixtures of hexanes or heptanes.

Although the preferred extraction solvent for obtaining the oat oil is hexanes or a similar paraffin solvent, extraction of bound lipids (phospholipids, glycolipids and, possibly, antioxidants) from oats with relatively more polar organic solvents such as ethanol will allow isolation of these potentially beneficial substances which have potential uses as sources of antioxidants, emulsifiers, and therapeutic agents for skin care.

The crude oat oil recovered from the solvent extraction is simply washed with either water or phosphoric acid and then is subjected to an optional low temperature (15° C.–120° C.) vacuum deodorization step. The freshly isolated oil has a peroxide value of close to zero for up to about 50 days at 60° C. Through use of the low temperature vacuum deodorization step, an oil which is readily absorbed by the skin is obtained. In contrast, oat oil subjected to high temperature deodorization is not as easily absorbed by the skin and leaves a greasy feeling, similar to mineral oil or petrolatum.

Antioxidants are important in skin care products since a major cause of photoaging is believed to be uncontrolled lipid oxidation or peroxidation in the skin. Indeed, some experts expect that normal, non-sun-induced aging may be attributable to oxidation. Lipid peroxidation is caused by the generation of free radicals when photons of ultraviolet light strike the skin. These radicals cause damage to vital skin components and also induce localized inflammatory responses.

An interesting and unexpected feature of the oat oil compositions of the invention is the ability of the compositions to inhibit lipid peroxidation in response to ultraviolet radiation. When applied to the skin prior to ultraviolet irradiation, the oat oil compositions of the invention significantly inhibit peroxidation of skin lipids during the irradiation. This property is interesting both for its obvious indication of the compositions of the invention in sun protectant formulations as well as general dermatological compositions. It is expected that if skin lipid oxidation or peroxidation is a pinnacle or an involved event in skin aging, the compositions of the invention are well tailored to fill the needs in the art.

Intriguingly, the use of more extensively purified preparation of oat oil has been shown to have deleterious effects upon the antioxidant properties of the oat oil. In particular, alkaline neutralization appeared to cause coprecipitation of the antioxidants in the oil with the fatty acids. While this property is beneficial in oat oil soap making as discussed in Example 7, it is not desirable where the oil is to be used neat, i.e., directly in a composition or formulation.

Accordingly, the skin lipid peroxidation-inhibiting effect of the compositions of the invention has extensive utility in the cosmetic arts for protecting skin from oxidative damage, or events, such as caused by ultraviolet irradiation. This damage includes skin cancer as well as premature aging of the skin.

Oat oil can be used either alone or in conjunction with any of the commercially available ultraviolet blocking agents including p-aminobenzoic acid (PABA), titanium dioxide ($TiO_2$), Avobenzone (1-(p-tert-butylphenyl)-3-(p-methoxyphenyl)-(3-propanedione), Lisadimate (glycerol-1-(p-aminobenzoate), Roxamidate (ethyl-4- [bis-(2-hydroxypropyl)amino]benzoate), actinquinol (8-ethoxy-5-quinolinesulfonic acid), β-carotene, cinoxate (2-ethoxymethyl p-methoxycinnamate), 4-(dimethylamino) benzoic acid, dioxybenzone (2,2'-dihydroxy-4-methoxybenzophenone), lawsone (2-hydroxy-1,4-naphthoquinone, mexenone (2-hydroxy-4-methoxy-4'-methyl-benzophenone), octabenzone (2-hydroxy-4-(octyloxy)benzophenone), sulisobenzone (5-benzoyl-4-hydroxy-2-methoxy-benzene-sulfonic acid), and homoethyl salicylate (2-hydroxybenzoic acid ethyl ester) are all well known sunscreen or sun blocking materials that can be used as sunscreen agents in the present invention. Other sunscreen agents, UV blockers, and/or screens can also be used to provide a better barrier against ultraviolet irradiation-induced skin damage.

The oat oil compositions of the invention can also be formed into an emulsion with an aqueous phase and an emulsifier. The emulsifier can be a conventional emulsifier or can be a proteinaceous particulate material, such as those described in U.S. patent application Ser. Nos. 07/505,126 and 08/031,611, the disclosures of which are hereby incorporated by reference. Particularly preferred proteinaceous emulsifiers are the MICROAT™ proteinaceous emulsifiers, available from NURTURE, Inc., Missoula, Mont. The use of other natural and synthetic emulsifiers, including the synthetic compounds laureth-4, steareth-10 and PEG-5 lauramide is also within the scope of the present invention.

In accordance with the present invention, the oat oil compositions are preferably included as a major portion of the formulation. The oil compositions can be thickened using a small percentage of thickener. Accordingly, the incorporation of the oat oil compositions into formulations including creams, pastes, gels, and lotions by well known methods is contemplated. It should be stressed that unlike a majority of conventional sunscreen or sunblock constituents, such as p-aminobenzoic acid (PABA), oxybenzone, and the like, or many conventional antioxidants included in cosmetic formulations, the oat oil compositions of the invention are natural sunscreen or sunblock agents and antioxidants. Thus, the use of the oat oil compositions of the invention will assuage the public's concerns about the use of synthetic materials in cosmetic products.

As will now be appreciated, the oat oil compositions of the invention are relatively easy to produce, and are prepared from a commodity product that is widely available. Thus, the compositions of the invention are amenable to widespread manufacture and use. Moreover, the oat oil compositions do not have any disagreeable odors, are not irritating to the skin, and are nontoxic. Some synthetic sunblock agents, most notably PABA, are quite irritating to individuals allergic to this compound. Furthermore, since the oat oil compositions are completely natural products, there is no requirement for extensive FDA testing prior to their use.

Another application of the oat oil compositions of the invention is in the production of a mild, nongreasy soap. This soap has beneficial antioxidant properties and is prepared by a cold saponification process using the oat oil formulations of the invention mixed with a stoichiometric amount of 50% aqueous sodium hydroxide. Since a significant amount of heat is generated during saponification, a cooling apparatus may be required. While a cooling apparatus is generally not required for making small batches of soap since limited heat is generated, it is expected that larger scale production will likely necessitate the use of a cooling apparatus, for example heat exchangers and the like. The soap has a pleasant odor, produces a good level of suds in both hard and soft water and rinses easily without leaving a film. The soap cleans well and leaves the skin feeling soft and smooth. In addition, this soap was determined to be less destructive to the outer layer of the skin (stratum corneum) than the benchmark IVORY® soap. Thus, a highly beneficial and nonirritating soap can be produced in accordance with the invention.

Further details, objects, and advantages of the present invention will be evident from the following examples. It will be understood, however, that the examples are illustrative, rather than limiting.

An oat oil composition of the present invention was extracted and water or phosphoric acid-washed as described in the following example.

EXAMPLE 1

Isolation of Oat Oil

For extraction experiments, Tibor oats, a patented strain developed by Agriculture Canada, were ground into a coarse flour using a pin mill. Extractions were conducted in flasks or beakers of 500 ml or larger volume. One part oat flour was mixed with 2.5 to 3 parts hexanes by weight, at either ambient or elevated temperatures. The solids were then separated by centrifugation and the solvent was removed by warming gently under vacuum. 100–200 g flour could be extracted at a time using this method. The hexanes extract was a cloudy, viscous oil similar to most crude vegetable oils and the yield of oil at both 23° C. and 69° C. was about 6% of the flour weight.

The oil was heated in a jacketed tank to 70–75° C. Three percent by weight soft water at 80° C. was then added and the mixture was agitated for 30 minutes. The oil was then centrifuged to remove solid material, which consisted primarily of starch and protein. A sample of the clarified oil was centrifuged and found to contain 1.3 wt % solids. The clarified oil was heated again to 70°–75° C., mixed with 2 wt % soft water for another 30 min, and centrifuged. The clarified oil from the second wash contained no solids. The oil was heated under vacuum to 100°–105° C. in a reactor, held for 15 min to dry, cooled to 60° C. and packaged under nitrogen.

Duplicate samples of water-washed oat oil were washed with 0.002 parts U.S.P. grade phosphoric acid and 0.003 parts 50% citric acid solution, respectively. In each case, carbon dioxide was bubbled through the oil for 1 min and the oil-acid mixture was heated to 60° C. under a carbon dioxide atmosphere and maintained at 60° C. for 1–2 hours. About 0.2 parts deionized water was then added with stirring, and the oil was centrifuged to remove the solids and the aqueous phase. Multiple filtrations through sodium sulfate yielded clear oils. The odor and taste of the resulting oils were similar to those noted before acid washing.

This crude oat oil was added to canola oil to determine whether it could, by virtue of its antioxidant properties, extend the shelf-life of the canola oil as described in the following example. cl EXAMPLE 2

Stabilization of Canola Oil by Addition of Oat Oil

When oat oil prepared in Example 1 was added to canola oil, the shelf life of the canola oil was greatly extended as measured by the peroxide value. The peroxide value was determined by the iodometric technique described in the American Oil Chemists' Society Method Cd 8–53 (*Oil and Soap* 9:89, (1932); *J. Assoc. Off. Anal. Chem.* 75:507 (1992)). The oil was dissolved in a mixture of chloroform and acetic acid and mixed with potassium iodide (KI). The peroxides in the oil converted the iodide to iodine, which was then backtitrated with sodium thiosulfate.

Oat oil was added to the canola oil at 5%, 10%, and 20% concentrations and the samples were allowed to stand at 35° C. Samples were tested at 7 days and storage was continued at 35° C. with additional testing at 13, 24, 31, 38, 77 and 133 days. The samples were titrated as follows.

Five grams of oil was mixed with 30 ml of a 3:2 acetic acid-chloroform solution. Saturated KI (0.5 ml) was then added and the solution was incubated for exactly one minute with occasional shaking followed by addition of 30 ml distilled water. The sample was then titrated with 0.1 N sodium thiosulfate until the yellow iodine color had almost disappeared. About 0.5 ml starch indicator solution (1 g starch in small amount of cold water added to 200 ml boiling water, boiled for several seconds and cooled) was added and the titration was continued with constant agitation, especially near the end point, until the blue color just disappeared. A blank determination (no oil) was also conducted. The peroxide value (milliequivalents peroxide/1000 g sample) was calculated from the following equation:

$$\frac{(S-B) \times N \times 1000}{\text{wt. of sample}}$$

Where

B=titration of blank (ml)

S=titration of sample (ml)

N=normality of sodium thiosulfate solution

The results of the addition of oat oil to canola oil are summarized in Table 1. As indicated in the Table, the addition of as little as 5% oat oil significantly extended the canola oil's shelf life, while 20% oat oil extended the shelf life by about three months.

TABLE 1

| Peroxide Value of Canola Oil With and Without Added Oat Oil | | | | |
| --- | --- | --- | --- | --- |
| Days Stored at 35° C. | Neat Canola Oil | 5% Oat Oil | 10% Oat Oil | 20% Oat Oil |
| 7 | 0 | 0 | 0 | 0 |
| 13 | 0 | 0 | 0 | 0 |
| 24 | 1 | 0 | 0 | 0 |
| 31 | 2 | 0 | 0 | 0 |
| 38 | 10 | 0 | 0 | 0 |
| 77 | 118 | 56 | 6 | 0 |
| 133 | 337 | 298 | 89 | 22 |

In many deodorization techniques, oils are heated to a relatively high temperature. In order to determine if conventional deodorization techniques limited the antioxidant effectiveness of the oat oil, we conducted experiments involving low temperature vacuum deodorization.

EXAMPLE 3

Increase in oat oil stability after low temperature vacuum deodorization

In a first experiment, water-washed oat oil was subjected to vacuum at room temperature (23° C.). After about 1–2 hours, during which a great deal of outgassing occurred and the pressure remained above 5 mm Hg, it was possible to reduce the pressure to 500 μm Hg. After about 4 hours the bubbling stopped and the pressure held steady at 200 μm. When applied to the skin, this oil was easily absorbed. A sample of this oil was stored at 62° C. in a loosely-stoppered container. After 102 days of storage, the oil still had a peroxide value of zero.

In a second experiment, water-washed oat oil was subjected to vacuum at room temperature until the pressure stabilized at 150 μm Hg and the bubbling stopped (about 4 hours). The oil was then heated to 100° C. and held at this temperature for 1 hour at which time the pressure was 200 μm Hg. The sample was then cooled to room temperature under vacuum. When applied to the skin, this oil was easily absorbed. A sample of this oil was put into storage at 62° C. in a loosely-stoppered container. After 28 days of storage, its peroxide value was still zero. Vacuum deodorization of oat oil at temperatures between about 15° C. and about 120° C. is contemplated.

Vacuum deodorization at higher temperatures (about 250° C.) resulted in diminished antioxidant effectiveness and the resulting oil was poorly absorbed by the skin. Accordingly, it appears as though high temperature deodorization removes some of the antioxidant activity from the oat oil. Use of lower temperature deodorization clearly produces an oil with prolonged antioxidant activity.

As a model to determine the effectiveness of the oat oil compositions of the invention in inhibiting lipid peroxidation in response to exposure to ultraviolet radiation, we prepared mixtures of the oat oil compositions with linoleic acid. Linoleic acid forms peroxides readily upon exposure to UV radiation. Therefore, we expected that the oat oil compositions would inhibit the peroxidation of the linoleic acid.

EXAMPLE 4

Inhibition of lipid peroxidation in vitro

Linoleic acid of 65% purity was used as neat linoleic acid (Barnett Products, Englewood Cliffs, N.J.). Neat oat oil was provided by NURTURE, Inc. (Missoula, Monn.). Samples were used neat (100%), 5%, 10% and 25% and were dissolved in reagent grade ethanol prior to use (except the neat product). Samples were prepared in petri dishes and charged with 10 ml of the test products.

The two oils were diluted and arranged linearly under the 290–320 nm UVB light source, with the radiometer detector placed in the center of the test specimens. An average of 2 Joules per hour of UVB irradiation was administered and aliquots were taken every hour for five hours. A 0.5 ml aliquot was taken before UVB irradiation was performed. Production of malonyldialdehyde (MDA), an indicator of lipid peroxidation, was determined by the thiobarbituric acid method (Mihara et al., (1980) *Biochem. Med.*, 23:302–311).

Briefly, 0.5 ml sample, 2.5 ml 1% phosphoric acid (pH 2.0) and 1.5 ml 0.8% aqueous thiobarbituric acid was placed in a 15 ml glass tube and capped with a marble. The mixture was heated in a boiling water bath for 30 minutes, cooled to room temperature for about 30 minutes and extracted with 2 ml n-butanol. The butanol phase was separated by centrifugation at 14,000×g at 4° C. for 15 min and the absorbance was taken at 535 nm using a Model 690 spectrophotometer (Sequoia Turner Corp., CA). The standards used were 0, 1.0, 2.5, 5.0, 7.5 and 10 nanomoles/tube of MDA prepared from 1,1,3,3-tetramethoxypropane (TMP) using the same reaction as above substituting the TMP for the lipid. The amount of MDA is calculated as follows.

$$nmoles\ MDA = \frac{volume \times absorbance\ at\ 535\ nm}{\Sigma \times 10^{-1}}$$

where $\Sigma$ = coefficient for MDA (1.5)

$$Extinction = \frac{nmoles\ MDA}{100\ \mu g\ lipid}$$

The results are summarized in Table 2. The data indicate that oat oil is moderately effective in inhibiting UV-induced lipid peroxidation in vitro at a low level (5–10), and is highly effective at 254. At 5%, oat oil inhibits peroxidation by UV light for 2 hours, while at 10% this inhibition extends for 3 hours. The antioxidants in the oat oil most likely exert their effects by acting as free radical scavengers, thus sequestering the catalysts necessary to promote effective lipid peroxidation.

TABLE 2

MDA assay of UVB-irradiated oat oil and linolenic acid
Determination of Peroxide Value (Malonyldialdehyde
assay) on Oat Oil (OO) and Linoleic Acid 65% (LA), neat, 5%,
10%, and 25% in Ethanol. Absorbance at 535 nm - %
Concentration vs. Time (hours)

| PRODUCT | TIME (hrs) | NEAT (100%) | 5% | 10% | 25% |
|---|---|---|---|---|---|
| LA | 0 | 0.551 | 0.195 | 0.205 | 0.334 |
| OO |   | 0.159 | 0.086 | 0.086 | 0.128 |
| LA | 1 | 1.059 | 0.510 | 0.783 | 1.313 |
| OO |   | 0.200 | 0.215 | 0.230 | 0.217 |
| LA | 2 | 1.552 | 1.044 | 1.549 | 2.273 |
| OO |   | 0.183 | 0.296 | 0.327 | 0.294 |
| LA | 3 | 2.101 | 2.078 | 2.370 | 2.520 |
| OO |   | 0.242 | 0.983 | 0.489 | 0.261 |
| LA | 4 | 3.051* | 2.495 | 2.560 | 2.418 |
| OO |   | 0.276 | 1.595 | 1.224 | 0.478 |
| LA | 5 | 2.273 | 2.303 | 2.495 | 2.472 |
| OO |   | 0.435 | 0.498 | 0.450 | 0.281 |

*Contaminated sample

To determine whether the oat oil compositions of the invention were effective in inhibiting skin lipid peroxidation, the following experiments were performed.

EXAMPLE 5

Inhibition of lipid peroxidation by oat oil in vivo

The method used was similar to the procedure outlined by the FDA in the OTC Monograph on Sunscreen Products (10). The solar simulator (Solar Light Company, Philadelphia, Pa.) consisted of a 150 watt compact arc xenon burner with a power supply, an ignitor and filters. Infrared radiation was attenuated with Corning black glass (Corning Industries, Corning, N.Y.) plus a dichroic mirror. Short wave ultraviolet rays were eliminated by external filtration with a 1 mm thickness WG 320 glass (Schott Filter Co., Duryea, Pa.). The radiation output was measured with a portable R-B meter before and after testing.

On the day of the study, subjects reported to the laboratory. The volar forearm (palm side) was used as the test site. A 0.1 ml amount of either oat oil or 65% linoleic acid was applied to different sections of the volar forearm and spread evenly. One area was left untreated as a control. Exposure time was determined for each subject based on their MED (minimal erythemal dose, the amount of irradiation one can receive before the skin just starts to redden). Each subject was irradiated for 2 MEDs. Five hours later, lipids were extracted from the volar forearm at ambient temperature. A glass cylinder was placed on the volar forearm and 1 ml isopropyl ether was pipetted onto the skin which was then gently agitated for 1 minute using the glass rod. The extract was transferred to a test tube and the isopropyl ether evaporated under a stream of nitrogen. The lipid residue from the extracts was dissolved in 1 ml ethanol and used for the MDA assay as described in Example 4. The results are summarized in Tables 3 and 4 below.

TABLE 3

TOTAL LIPIDS/MDA*

| Subject Initials | Test Products** | nM MDA | µg 20 µl Lipid*** | nM MDA/ 100 µg Lipid |
|---|---|---|---|---|
| BH | Control | 7.0 | 25 | 28.00 |
|  | Oat Oil | 6.2 | 60 | 08.68 |
|  | Linoleic Acid | 6.2 | 30 | 20.46 |
| JP | Control | 13.0 | 30 | 43.89 |
|  | Oat Oil | 8.5 | 25 | 34.00 |
|  | Linoleic Acid | 11.2 | 25 | 44.80 |
| JV | Control | 7.8 | 30 | 25.74 |
|  | Oat Oil | 6.5 | 25 | 26.00 |
|  | Linoleic Acid | 13.0 | 25 | 52.00 |

*2 MED's of irradiation
**Control (untreated irradiated), Oat Oil (neat), Linoleic Acid 65% (neat)
***Lipid extracted from the skin

TABLE 4

TOTAL LIPID/MDA VALUES

|  | Control | Oat Oil | Lin. Acid |
|---|---|---|---|
|  | 28.00 | 08.68 | 20.46 |
|  | 43.89 | 34.00 | 44.80 |
|  | +25.74 | +26.00 | +52.00 |
| TOTAL | 97.63 | 68.68 | 117.26 |
| MEAN | 32.54 | 22.89 | 39.09 |

Figure 5:
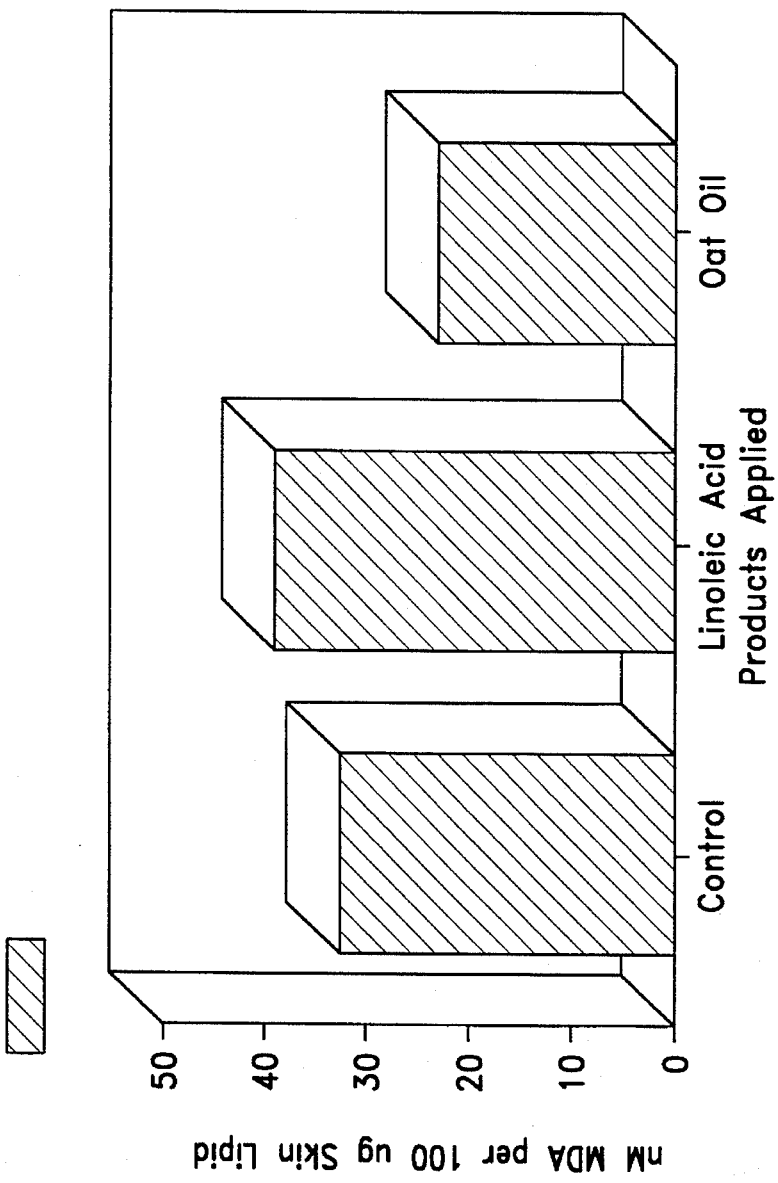
FIG. 5 summarizes the in vivo lipid peroxidation study. The oils used are shown on the x-axis and the amount of MDA per 100 µg skin lipid is shown on the y-axis.

The results of Table 4 are summarized in FIG. 5. The data demonstrates that neat oat oil is highly effective in reducing peroxidation of skin lipids following ultraviolet irradiation. A reduction of 30% was obtained with oat oil over the untreated control as compared to a 20% increase seen with linoleic acid.

EXAMPLE 6

Oat Oil-Based Sunblock Cream Emulsion

A stable sun protectant formula was prepared in the following manner. The ingredients listed below in Table 5, were mixed in a vessel.

TABLE 5

| Ingredient | Percent | Function | Supplier* |
|---|---|---|---|
| Oat Oil | 5.0% | Emollient | Nurture |
| Ceraphyl GA-D | 1.0% | Emollient | Van Dyk |
| Arlacel 165 | 2.5% | Co-emulsifier | ICI |
| Brij 35 | 2.0% | Co-emulsifier | ICI |
| Finsolv TN | 15.0% | Spreading Agent | Finetex |
| Silicone 225 | 2.0% | Moisturizer | Dow Corning |
| Proteinaceous Particulate | 15.0% | Protectant, Emulsifier, Film Former | Nurture, Inc. |
| $TiO_2$ | 6.0% | Sunscreen | Creative Polymers |
| Water | 50.3% | Carrier/Solvent |  |
| Keltrol | 0.2% | Stabilizer | Kelco |
| Germaben IIe | 1.0% | Preservative | Sutton Labs |

*The Suppliers abbreviated in the Table are: Creative Polymers, New Brunswick, NJ, Dow Corning, Midland, MI, Finetex, Elmwood Park, NJ, ICI Americas, Inc., Wilmington, DE, Kelco Co., San Diego, CA, Nurture, Inc., Missoula, MT, Sutton Laboratories, Inc., Chatham, NJ, Tri-K Industries, Emerson, NJ, Van Dyk & Co., Belleville, NJ.

The mixture was then agitated at 25° C. to form a smooth, creamy textured, viscous fluid emulsion. This emulsion was very smooth to the touch and, when rubbed on the skin, dried to form a thin film that was neither oily nor greasy to the touch. Moreover, when dried, the film was not easily rubbed off and could withstand immersion in water. The oat proteinaceous material acts as the emulsifying agent (the "proteinaceous emulsifying agents" or "proteinaceous particulate materials"), allowing the creation of an emulsion that can dry to form a thin film on the skin. These proteinaceous emulsifiers are totally natural and extremely safe to use.

It is often desirable to add certain other components to the emulsion formulations. For example, a preservative is included to inhibit the growth of microorganisms. Particularly useful preservatives include certain quarternium compounds, such as DOWICIL® 200 (Dow Chemical, Midland, Mich.), and parabens such as GERMABEN® IIE (Sutton Laboratories, Inc., Chatham, N.J.). Also, in certain applications, it is preferred to add additional natural or synthetic moisturizing agents such as jojoba oil (Tri-K industries, Emerson, N.J.) and dimethicones or cyclomethicones such as Silicone 200 or Silicone 345 (Dow Corning, Midland, Mich.), respectively.

The lipophilic phase is believed to act as an emollient. Oat oil, in particular, produces a very rich and creamy emulsion. Moreover, formulations prepared through the use of oat oil have the desirable quality of oat oil's natural antioxidant effects. In addition, certain other emollients may be used to promote increased adhesion of the formulation, for example, or other desired effects. For instance, in a preferred embodiment of the present invention, Ceraphyl GA-D, a soybean oil maleate, was used (Van Dyk & Co., Belleville, N.J.). Furthermore, in certain preferred embodiments, coemulsifiers may be used for maintaining stability. For example, we use ARLACEL® 165 (a polyoxyethylene glycol stearate) and BRIJ® 35 (a polyoxyethylene lauryl ether) (ICI Americas, Inc., Wilmington, Del.) as coemulsifiers. Spreading agents are also useful supplements for the formulations of the present invention, such as FINSOLV® TN, a $C_{12}$ to $C_{15}$ alcohol benzoate (Finetex, Elmwood Park, N.J.). A variety of stabilizers can also be used to maintain the viscosity of the formulation over time. For example, xanthan gums, such as KELTROL® (Kelco Co., San Diego, Calif.), are suitable stabilizers.

Waterproofing agents are also desirable additives. Such agents enhance the abilities of the compositions on a surface to be submerged in water and continue to bind to the surface and substantially retain the bulk of the film and its skin protective qualities. Examples of suitable waterproofing agents are acrylate-t-octyl acrylamide copolymer (such as DERMACRYL® 79, National Starch & Chemical Co., Bridgewater, N.J.); polyvinylpyrolidinone/eicosene copolymer (such as GANEX®, GAF Corp., New York, N.Y.); and dimethicone, a mixture of fully methylated linear siloxane polymers end blocked with trimethylsiloxy units (such as Dow Corning 200 fluid, Midland, Mich.).

Sunscreen formulations according to the present invention may be prepared having a variety of sun protection factor (SPF) values. An SPF value is defined as the UV energy required to produce a MED of protected skin divided by the energy required to produce an MED on unprotected skin. This SPF system essentially allows the calculation of the additional time that a person wearing a sunscreen product can remain in the sun without burning. As such, an SPF of 2 allows a user to stay in the sun twice as long, whereas an SPF of 15 increases the time to 15 times as long.

Sunscreen formulations according to the present invention may be prepared having a variety of SPF values. The SPF can be affected by increasing or decreasing the percentage composition of the proteinaceous particulate and other UV blocking materials.

Due to the beneficial antioxidant properties of oat oil, it was envisioned that a soap containing oat oil would have many beneficial dermatological properties. Oat oil-containing soap was prepared as described in the following example.

EXAMPLE 7

Production of Oat Oil Soap

Water-washed oat oil was used to make soap by a cold saponification process. In this process, oat oil was mixed with a stoichiometric amount of 50% aqueous sodium hydroxide. After 15–30 minutes of stirring, the mixture was poured into molds and allowed to cure for 1–2 days. The soap was then removed from the molds and sliced into cakes (70–100 g each) and allowed to continue curing. The saponification reaction was complete within one week as indicated by pH: within one week the pH of a 1% solution of the soap had reached a steady value of about 10.3. The soap was light yellow-brown in color and had a soapy odor with "oaty" or "cereal" overtones.

This soap was used by a group of Nurture, Inc. employees in a home use test. The soap produced a good level of suds in both hard and soft water and rinsed easily leaving no film. The soap was considered a good cleaner by most users and yet left the skin feeling soft and smooth.

A cross-section was cut from the middle of a bar of two-week-old cold-saponified soap and its peroxide value was determined to be 0.0. This is consistent with the hypothesis that alkaline neutralization precipitates antioxidants without destroying or inactivating them. The fatty acids in the soap exhibited no peroxidation after two weeks' storage, although alkali-refined oat oil has a measurable peroxide value after being stored for the same length of time.

The cold saponification process yielded soap already formed into cakes without a pressing operation, and the process was much faster and less laborious than the hot process commonly used in the soap-making industry. Moreover, cold saponified soap contained all the phospholipids, sterols and other unsaponifiable lipids, and all the glycerol liberated by the saponification reaction. All of these ingredients are potentially beneficial to the skin, particularly the phospholipids, glycerol, and antioxidants. In addition, fragrances and additional moisturizers may be added.

Soap prepared in accordance with the present invention is highly dermatologically effective. The term "dermatologically effective" is used herein to describe the moisturizing, mildness, rinsability, non film-forming nonirritating, and/or low levels of destruction of the stratum corneum properties associated with the oat oil composition based soaps.

Since a thickened oat oil-containing gel for skin-care applications requiring such a composition will also be beneficial, a gel was made using sodium and calcium soaps derived from oat oil and light mineral oil as described below.

EXAMPLE 8

Production of oat oil-containing gel

Certain paraffin oils, when mixed with fatty-acid soaps and heated, form thick gels that form metastable greases when cooled. Two oat soaps were used in combination with light mineral oil (Drakeol 5®, Penreco). to make a thickened grease. Oat soap made by the cold saponification process (6 g) was mixed with 60 g Drakeol 5®and heated to 110° C. with stirring. Some of the soap dissolved, while the remainder settled to the bottom of the beaker as soon as the stirring had stopped. The liquid layer was decanted, then heated to 170° C. with stirring. The resulting clear liquid was cooled. At 120° C., the liquid had gelled fairly well, and at room temperature the product became a stiff viscoelastic jelly. After overnight storage (about 16 hours) at room temperature, the jelly appeared stable, although after 24 hours it began to separate into solid and liquid phases.

A calcium soap was made by treating cold saponified oat soap with calcium chloride. The calcium soap (3.4 g) was mixed with 59 g Drakeol 5®. This mixture was stirred to form a slurry, then heated with stirring. At about 90° C., the slurry began to thicken noticeably. At about 110° C., vigorous bubbling was observed, and after several minutes the slurry cleared rapidly. The stirring was continued while the liquid was allowed to cool. As the liquid cooled, some floc appeared and settled to the bottom. The sample was allowed to stand overnight, then 10 g calcium soap was added and the mixture was heated to 140° C. with stirring. The mixture was allowed to cool, at which time a very firm, brittle gel formed which appeared stable, but within a few days showed extensive syneresis.

The limited stability of these two gels is not an insurmountable problem since the production of a stable gel or grease usually requires adjustment of both formula and process parameters.

To determine other emollient and therapeutic properties of oat oil and oat soap, the rate of water loss through the skin was determined as described below.

EXAMPLE 9

Determination of Transepidermal Water Loss

Water loss through the skin (referred to herein as "transepidermal water loss" or "TEWL") is a function of the skin lipid barrier, the skin temperature and the external environment, such as humidity. Intrinsic characteristics of the skin may affect the rate of water loss by changes in the activation energy required for water transport. Water loss from the skin is proportional to the water content of the stratum corneum.

The subjects for this study were male and female volunteers aged 20 years or older. Subjects were free of any systemic or dermatological disorders which may have interfered with the integrity of the study. Subjects were not taking any medication, with the exception of birth control pills. The test products, oat oil and oat soap, were manufactured by Nurture, Inc., Missoula Mont., in accordance with Examples 1 and 7, respectively.

The method employed for the detection of water loss from the skin was a Dew Point Analyzer in a closed system. This consisted of a source of ultrapure dry nitrogen (Airco Products) at 5 psi connected to a flow meter (Dwyer) regulated at 120 cc/min. The nitrogen was conducted into a plastic cylinder with a cross sectional area of 2.835 cm$^2$ and then into the Dewpoint Analyzer (General Eastern Model 1311 DR Optical Dewpoint Sensor) attached to a Model 1500 Hygrocomputer. The flow rate of the effluent nitrogen was monitored by an identical Dwyer flow meter.

Seven sites on the subjects' volar forearm were used. 0.2 ml of 10% oat oil in canola oil, 20% oat oil in canola oil, 100% oat oil, 100% canola oil, 10% ivory soap, 10% oat soap and VASELINE® were used as the test materials. The subjects were placed in the test environment and allowed to come to equilibrium for at least 30 minutes. The base rate was determined on the volar forearm by attaching the probe and allowing the subject to come to equilibrium with the gas flow for at least 15 minutes. Three readings were taken, one minute apart which indicates whether the subject had come to equilibrium. If the readings continued to change in either direction, the subject was rechecked in 10 minutes. TEWL rates were measured in units of mg water loss/cm$^2$ of skin per hour (Table 6). The values represent the percent reduction of TEWL of the treated site over the control site. A negative value indicates that the product was effective in reducing the normal water loss from the skin. The normal rate of water loss in adults is about 0.5 mg/cm$^2$/hr.

TABLE 6

TEWL Values

| Subject Initials | Vaseline | Oat Oil 100% | Canola Oil 100% | 10% Oat Oil | 20% Oat Oil |
|---|---|---|---|---|---|
| S. F. | −61.34 | −56.15 | −50.25 | −53.77 | −35.44 |
| C. R. | −76.24 | −22.29 | −41.70 | −10.70 | −14.70 |
| D. H. | −56.19 | −15.85 | −42.75 | −28.59 | −40.42 |
| T. D. | −54.40 | −53.17 | −46.60 | −50.43 | −43.70 |
| T. C. | −50.00 | −44.59 | −37.83 | −38.41 | −09.02 |
| MEAN | −59.63 | −38.41 | −43.83 | −36.38 | −28.66 |

| Subject Initials | Vaseline | 10% IVORY soap | 10% OAT soap |
|---|---|---|---|
| D. H. | −72.32 | (+17.34*) | −29.55 |
| C. S. | −81.31 | −24.63 | (−111.47*) |
| N. M. | −89.52 | −12.75 | −28.81 |
| T. B. | −85.14 | −07.39 | −18.92 |
| S. D. | −28.78 | −16.25 | −11.06 |
| MEAN | −71.41 | −15.26 | −20.86 |

Note - 10 and 20% oat Oil was made in Canola Oil.
*Values not used.

While particular embodiments of the invention have been described in detail, it will be apparent to those skilled in the art that these embodiments are exemplary, rather than limiting, and the true scope of the invention is that defined in the following claims.

What is claimed is:

1. A method for producing a cosmetic formulation comprising the steps of:

providing an aqueous phase;

providing a lipophilic phase comprising crude oat oil;

providing an amount of an emulsifier effective to form an emulsion of the aqueous phase and the lipophilic phase;

mixing the aqueous phase, the lipophilic phase, and the emulsifier to form a mixture;

agitating the mixture such that an emulsion is formed.

2. The method of claim 1, wherein said crude oat oil is produced by a process consisting essentially of:

contacting the oats with an organic solvent to extract oat oil;

evaporating the organic solvent from the oat oil;

washing the oat oil; and deodorizing the oat oil fraction under vacuum at a temperature below about 120° C.

3. The method of claim 2, wherein said solvent is hexane.

4. The method of claim 2, wherein said oat oil is washed with either water or phosphoric acid after the solvent evaporation step.

5. The method of claim 2, wherein said oat oil has a peroxide value of about zero for about 50 days.

6. The method of claim 1, wherein the emulsifier is a substantially chemically intact proteinaceous particulate material.

7. The method of claim 6, wherein the proteinaceous material is derived from seeds and the seeds are selected from the group consisting of legumes and grains.

8. The method of claim 7, wherein the seeds are selected from the group consisting of canola, beans, oats, rape seed, and soya.

9. The method of claim 1, wherein the oat oil is included in an amount effective to inhibit oxidation when applied to skin.

10. The method of claim 1, wherein the oat oil is included in an amount effective to inhibit lipid peroxidation in skin when applied to skin and the skin is exposed to ultraviolet irradiation.

11. The method of claim 1, wherein the oat oil is obtained from a crude oat oil fraction that is derived from the extraction of oats with an organic solvent.

12. The method of claim 11, wherein the organic solvent is an isomeric mixture of hexanes.

13. The method of claim 11, wherein the oat oil is washed with a reagent selected from the group consisting of water and an aqueous solution of phosphoric acid.

14. The method of claim 11, wherein the oat oil is derived from a crude oat oil fraction that has been subjected to low temperature vacuum deodorization.

15. A method of inhibiting skin lipid peroxidation in response to ultraviolet irradiation of the skin, comprising applying an oat oil composition to the skin then exposing the skin to ultraviolet irradiation.

16. The method of claim 15, wherein the oat oil has been obtained by extraction of oats with an organic solvent.

17. The method of claim 16, wherein the organic solvent is an isomeric mixture of hexanes.

18. The method of claim 15, wherein the oat oil has been derived from a crude oat oil fraction that has been washed with a reagent selected from the group consisting of water and aqueous solution of phosphoric acid.

19. The method of claim 15, wherein the oat oil has been derived from a crude oat oil fraction that has been subjected to low temperature vacuum deodorization.

20. The method of claim 15, wherein the oat oil is produced by a process consisting essentially of:

contacting oats with an organic solvent to extract oat oil;

evaporating the organic solvent from the oat oil;

washing the oat oil; and deodorizing the oat oil vacuum at a temperature below about 120° C.

21. A method of preparing a dermatologically effective soap, comprising cold saponifying a crude oat oil with alkali.

22. Crude oat oil prepared according to the process of claim 2.

23. In a crude oil isolated from oats, the improvement comprising:

(a) skin lipid peroxidation-inhibiting activity greater than linoleic acid; and (b) a peroxide value of zero for about 50 days.

* * * * *